(12) United States Patent
Viola

(10) Patent No.: US 8,246,575 B2
(45) Date of Patent: Aug. 21, 2012

(54) FLEXIBLE HOLLOW SPINE WITH LOCKING FEATURE AND MANIPULATION STRUCTURE

(75) Inventor: Frank J. Viola, Sandy Hook, CT (US)

(73) Assignee: Tyco Healthcare Group LP, Mansfield, MA (US)

( * ) Notice: Subject to any disclaimer, the term of this patent is extended or adjusted under 35 U.S.C. 154(b) by 776 days.

(21) Appl. No.: 12/372,080

(22) Filed: Feb. 17, 2009

(65) Prior Publication Data

US 2009/0216245 A1 Aug. 27, 2009

Related U.S. Application Data

(60) Provisional application No. 61/031,374, filed on Feb. 26, 2008.

(51) Int. Cl.
*A61M 31/00* (2006.01)
*A61M 37/00* (2006.01)
(52) U.S. Cl. .................................................. 604/95.04
(58) Field of Classification Search ............... 604/95.04, 604/528, 164.12, 165.01, 165.04, 170.03, 604/540
See application file for complete search history.

(56) References Cited

U.S. PATENT DOCUMENTS

| | | |
|---|---|---|
| 3,060,972 A | 10/1962 | Sheldon |
| 3,605,725 A | 9/1971 | Bentov |
| 3,625,200 A | 12/1971 | Muller |
| 4,054,128 A | 10/1977 | Seufert et al. |
| 4,327,711 A | 5/1982 | Takagi |
| 4,351,323 A * | 9/1982 | Ouchi et al. .............. 600/142 |
| 4,651,718 A | 3/1987 | Collins et al. |
| 4,655,257 A | 4/1987 | Iwashita |
| 4,686,963 A | 8/1987 | Cohen et al. |
| 4,776,844 A | 10/1988 | Ueda |
| 4,790,624 A | 12/1988 | Van Hoye et al. |
| 4,796,607 A | 1/1989 | Allred, III et al. |
| 4,838,859 A | 6/1989 | Strassmann |
| 4,841,951 A | 6/1989 | Umeda |
| 4,895,431 A | 1/1990 | Tsujiuchi et al. |
| 4,899,731 A | 2/1990 | Takayma et al. |
| 5,114,402 A | 5/1992 | McCoy |
| 5,143,085 A | 9/1992 | Wilson |
| 5,179,935 A | 1/1993 | Miyagi |
| 5,211,183 A | 5/1993 | Wilson |
| 5,238,005 A | 8/1993 | Imran |
| 5,251,611 A | 10/1993 | Zehel et al. |
| 5,271,381 A | 12/1993 | Ailinger et al. |
| 5,325,845 A | 7/1994 | Adair |
| 5,337,733 A | 8/1994 | Bauerfeind et al. |
| 5,345,937 A | 9/1994 | Middleman et al. |
| 5,349,964 A | 9/1994 | Imran et al. |

(Continued)

FOREIGN PATENT DOCUMENTS

DE 3039551 10/1981

*Primary Examiner* — Melanie Hand

(57) ABSTRACT

An apparatus is disclosed for introducing surgical instruments into a body cavity. The apparatus includes a series of interconnected segments configured to pivot relative to one another allowing an end effector to be steered into position. The apparatus is also capable of achieving a rigidized state wherein the interconnected segments are in high frictional contact with one another providing a stable platform for the manipulation of tissue. Tensile elements are attached to the end effector and a control member such that an operator may use the same control member to both rigidize the instrument and also to thereafter control the end effector.

13 Claims, 5 Drawing Sheets

U.S. PATENT DOCUMENTS

| | | |
|---|---|---|
| 5,357,979 A | 10/1994 | Imran |
| 5,381,782 A | 1/1995 | DeLaRama et al. |
| 5,394,864 A | 3/1995 | Kobayashi et al. |
| 5,415,633 A | 5/1995 | Lazarus et al. |
| 5,423,771 A | 6/1995 | Imran |
| 5,435,296 A | 7/1995 | Vivenzio et al. |
| 5,454,787 A | 10/1995 | Lundquist |
| 5,531,664 A | 7/1996 | Adachi et al. |
| 5,531,685 A | 7/1996 | Hemmer et al. |
| 5,624,380 A | 4/1997 | Takayama et al. |
| 5,624,381 A | 4/1997 | Kieturakis |
| 5,749,828 A | 5/1998 | Solomon et al. |
| 5,826,776 A | 10/1998 | Schulze et al. |
| 5,897,488 A | 4/1999 | Ueda |
| 5,904,657 A | 5/1999 | Unsworth et al. |
| 5,916,147 A | 6/1999 | Boury |
| 5,931,819 A | 8/1999 | Fariabi |
| 5,989,230 A | 11/1999 | Frassica |
| 5,997,526 A | 12/1999 | Giba et al. |
| 6,179,776 B1 | 1/2001 | Adams et al. |
| 6,210,337 B1 | 4/2001 | Dunham et al. |
| 6,270,453 B1 | 8/2001 | Sakai |
| 6,278,084 B1 | 8/2001 | Maynard |
| 6,323,459 B1 | 11/2001 | Maynard |
| 6,408,889 B1 | 6/2002 | Komachi |
| 6,447,478 B1 | 9/2002 | Maynard |
| 6,533,752 B1 | 3/2003 | Waram et al. |
| 6,610,007 B2 | 8/2003 | Belson et al. |
| 6,620,126 B2 | 9/2003 | Unsworth et al. |
| 6,638,268 B2 | 10/2003 | Niazi |
| 6,663,588 B2 * | 12/2003 | DuBois et al. ............. 604/95.04 |
| 6,786,864 B2 | 9/2004 | Matsuura et al. |
| 6,800,056 B2 | 10/2004 | Tartaglia et al. |
| 6,837,846 B2 | 1/2005 | Jaffe et al. |
| 6,887,235 B2 | 5/2005 | O'Connor et al. |
| 6,939,338 B2 | 9/2005 | Waldhauser et al. |
| 7,018,346 B2 | 3/2006 | Griffin et al. |
| 7,033,318 B2 | 4/2006 | Masunishi |
| 7,044,907 B2 | 5/2006 | Belson |
| 7,066,931 B2 | 6/2006 | O'Connor et al. |
| 7,090,637 B2 | 8/2006 | Danitz et al. |
| 7,169,130 B2 | 1/2007 | Exline et al. |
| 7,291,127 B2 | 11/2007 | Eidenschink |
| 2002/0068868 A1 | 6/2002 | Thompson et al. |
| 2002/0120178 A1 | 8/2002 | Tartaglia et al. |
| 2003/0083550 A1 | 5/2003 | Miyagi |
| 2003/0208219 A1 | 11/2003 | Aznoian et al. |
| 2004/0068161 A1 | 4/2004 | Couvillon et al. |
| 2004/0111009 A1 | 6/2004 | Adams et al. |
| 2004/0186350 A1 | 9/2004 | Brenneman et al. |
| 2004/0193008 A1 | 9/2004 | Jaffe et al. |
| 2004/0193009 A1 | 9/2004 | Jaffe et al. |
| 2004/0204676 A1 | 10/2004 | Anderson et al. |
| 2004/0210109 A1 | 10/2004 | Jaffe et al. |
| 2004/0220450 A1 | 11/2004 | Jaffe et al. |
| 2005/0085693 A1 | 4/2005 | Belson et al. |
| 2005/0119614 A1 | 6/2005 | Melsky |
| 2005/0250990 A1 | 11/2005 | Le et al. |
| 2006/0009678 A1 | 1/2006 | Jaffe et al. |
| 2006/0015009 A1 | 1/2006 | Jaffe et al. |
| 2006/0015010 A1 | 1/2006 | Jaffe et al. |
| 2006/0025652 A1 | 2/2006 | Vargas |
| 2006/0029531 A1 | 2/2006 | Breen et al. |
| 2006/0058582 A1 | 3/2006 | Maahs et al. |
| 2006/0064055 A1 | 3/2006 | Pile-Spellman et al. |
| 2006/0069346 A1 | 3/2006 | Smith et al. |
| 2006/0074383 A1 | 4/2006 | Boulais |
| 2006/0089532 A1 | 4/2006 | Tartaglia et al. |
| 2006/0111615 A1 | 5/2006 | Danitz et al. |
| 2006/0142732 A1 | 6/2006 | Karmakrkar et al. |
| 2006/0178560 A1 | 8/2006 | Saadat et al. |
| 2006/0211979 A1 | 9/2006 | Smith et al. |
| 2007/0005041 A1 | 1/2007 | Frassica et al. |

* cited by examiner

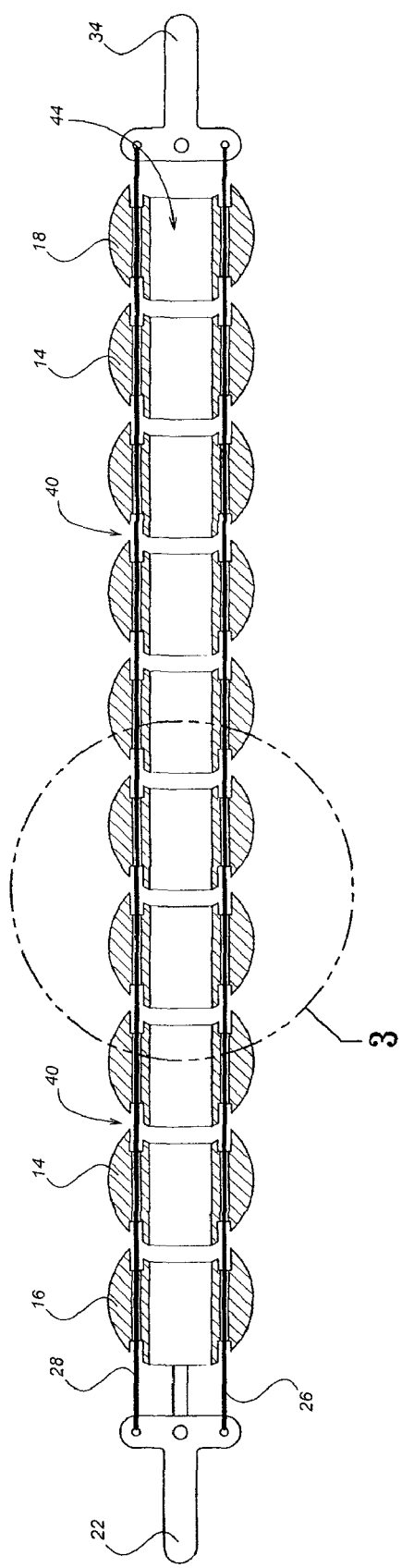
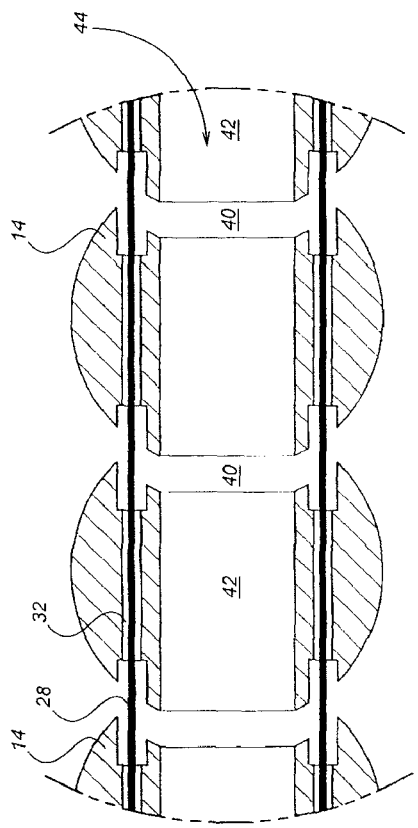
FIG. 2
FIG. 3

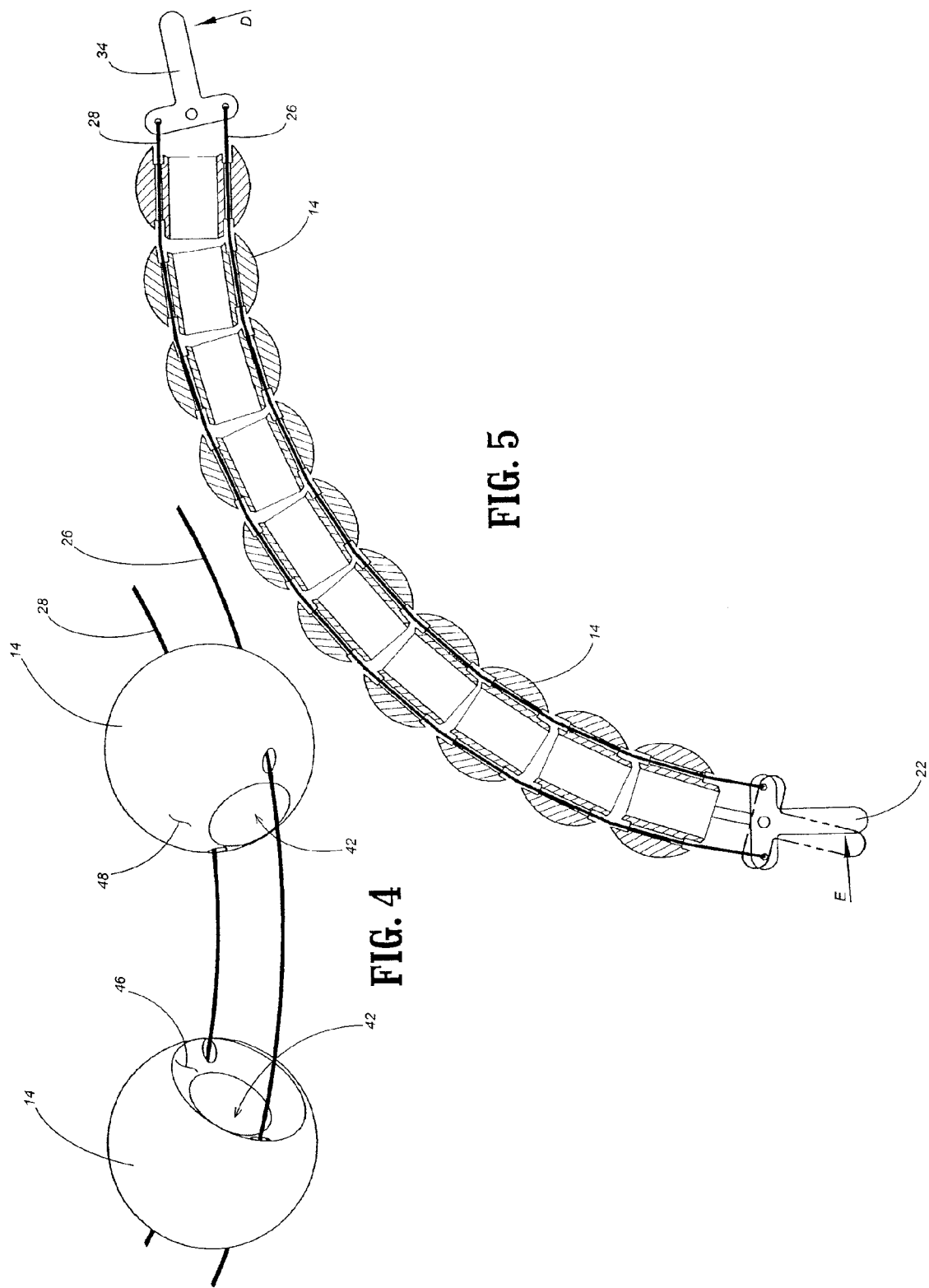

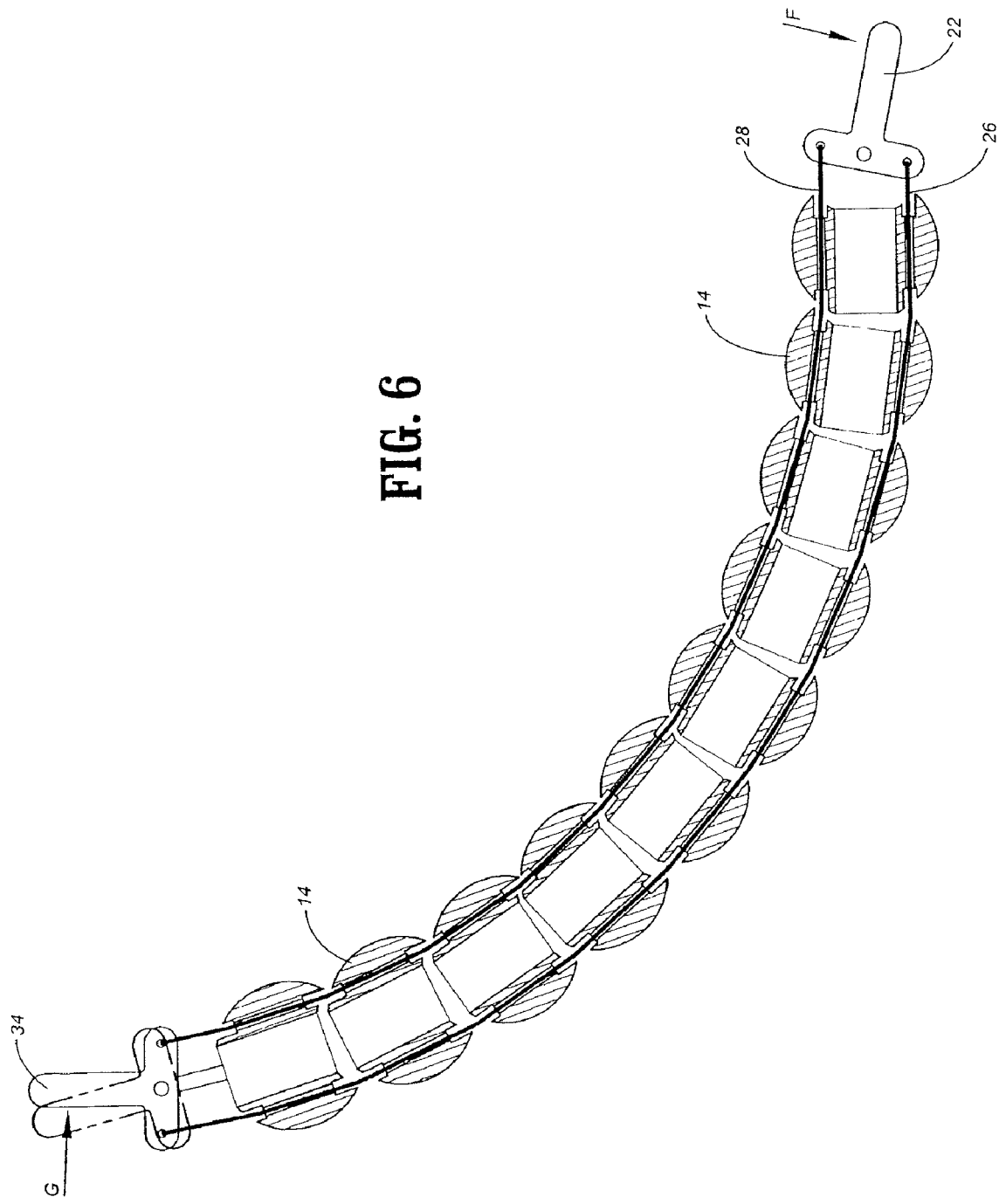

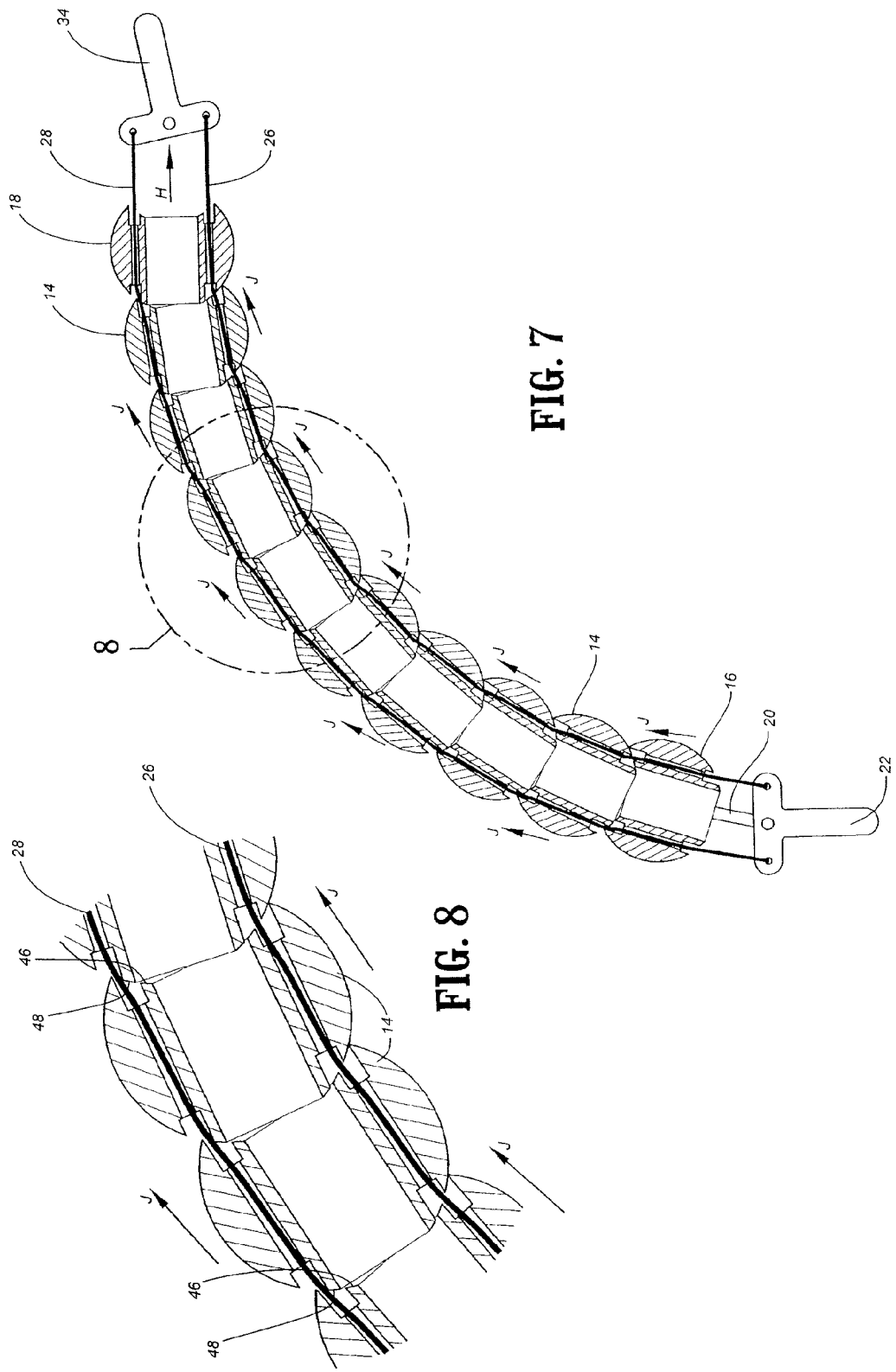

FLEXIBLE HOLLOW SPINE WITH LOCKING FEATURE AND MANIPULATION STRUCTURE

CROSS-REFERENCE TO RELATED APPLICATIONS

This application claims the benefit of and priority to U.S. Provisional Patent Application No. 61/031,374, filed Feb. 26, 2008, the entire disclosure of which is incorporated by reference herein.

BACKGROUND

1. Technical Field

The present disclosure relates generally to flexible steerable instruments, such as steerable catheters and/or probes which are remotely operated in endoscopic, endoluminal and laparoscopic procedures. In particular, the disclosure relates to a system and related methods for rigidizing a flexible steerable instrument and manipulating a distal tool on the rigidized instrument.

2. Background of Related Art

Surgical procedures such as laparoscopic, arthroscopic, and endoscopic procedures in general are termed minimally invasive at least in part because the incision required is relatively small, perhaps one inch in length or less. Small incisions are preferred because they are inherently less traumatic to the body tissue and subject internal organs to only a minimum of exposure to the contaminants in the outside atmosphere. Thus, small incisions enable shorter hospital stays and faster recoveries with less pain and scarring than is common with the larger incisions required for conventional surgery.

Endoscopic surgery is possible due in part to the availability of instruments designed specifically for this purpose. One such type of instrument, which may also be used for endoluminal procedures, is a flexible steerable instrument which may have a tool assembly (e.g., grasping jaws, cutting tools, camera, suction attachment, etc.) attached at the distal end. These instruments may be navigated and steered inside the patient's body using controls disposed on a proximal end of the instrument as the instrument is advanced into a body cavity such as the patient's bowel. Once in position, it is often desirable to maintain the particular position achieved by the instrument to facilitate tissue manipulation using the tool assembly.

Conventional flexible steerable instruments include two or more segments configured to pivot and/or swivel relative to each other. One or more tensile elements are coupled to the distal segment to allow the segments to be drawn into high frictional contact with one another thereby rigidizing the instrument. One drawback of the conventional flexible steerable instruments is that once rigidized the tensile elements are ineffective for controlling the distal tool. Any further manipulation of the tensile elements tends to alter the position achieved by the instrument. Therefore, to control the tool additional components must be incorporated increasing the cost, complexity and even the overall size of the instrument, which for example, can detract from the attendant advantages of endoscopic surgery. Accordingly, a need exists for a carrier apparatus including tensile elements adapted to both rigidize the apparatus and also to manipulate a surgical tool.

SUMMARY

The present disclosure describes a surgical apparatus for insertion into a body cavity. The apparatus includes an elongated flexibly body with an end effector disposed at a distal end of the body and a control member at a proximal end of the body. At least one pair of tensile elements is connected to the end effector such that a general tension applied to the pair of tensile elements tends to shift the instrument from a flexible condition to a rigid condition, while a differential tension applied to the pair of tensile elements tends to cause motion in the end effector. The motion in the end effector may be used to steer the apparatus into position and to manipulate tissue.

In some embodiments the elongated body may include a series of interconnected segments adapted to pivot relative to one another to give the instrument flexibility at least at a distal portion of the instrument. The segments may assume a substantially spherical shape with a concave surface on one end which interfaces with a convex surface on a neighboring segment. Each segment may include a cavity or throughbore which in combination with the cavities and throughbores in the remaining segments forms a central channel through all the segments. The segments may be forced into a high frictional contact by a general tension in the tensile elements to rigidize the apparatus. The general tension may be transmitted through the end effector and a support member connected to a leading segment to cause the high frictional contact that rigidizes the apparatus. The control member and the end effector may include a bell crank, which is connected to the tensile elements such that a pivotal movement of one bell crank effects corresponding pivotal movement in the other bell crank.

A method of operation is also disclosed. The distal end of an instrument may be inserted into a body cavity of a patient. An operator may steer the distal end of the instrument into a body lumen using a control member, rigidize a portion of the instrument, and thereafter manipulate the distal end of the instrument using the same control member used to steer the instrument into position.

BRIEF DESCRIPTION OF THE DRAWINGS

The accompanying drawings, which are incorporated in and constitute a part of this specification, illustrate embodiments of the present disclosure and, together with the detailed description of the embodiments given below, serve to explain the principles of the disclosure.

FIG. 2 is a top partial-cross-sectional view of the flexible steerable instrument shown in FIG. 1A depicting the instrument in a relaxed condition;

FIG. 3 is an enlarged view of the area of detail identified in FIG. 2;

FIG. 4 is a partial perspective view with parts separated of a central portion of the flexible steerable instrument shown in FIG. 1A depicting interfacing surfaces of the instrument;

FIG. 5 is a view similar to FIG. 2 depicting the instrument in a relaxed condition and biased to the right with respect to an operator;

FIG. 6 is a view similar to FIG. 2 depicting the instrument in a relaxed condition and articulated to the left with respect to an operator;

FIG. 7 is a view similar to FIG. 2 depicting the instrument in a rigid condition and articulated to the left with respect to an operator; and FIG. 8 is an enlarged view of the area of detail identified in FIG. 7.

DETAILED DESCRIPTION OF PREFERRED EMBODIMENTS

Figures 1A, 1B, 1C:
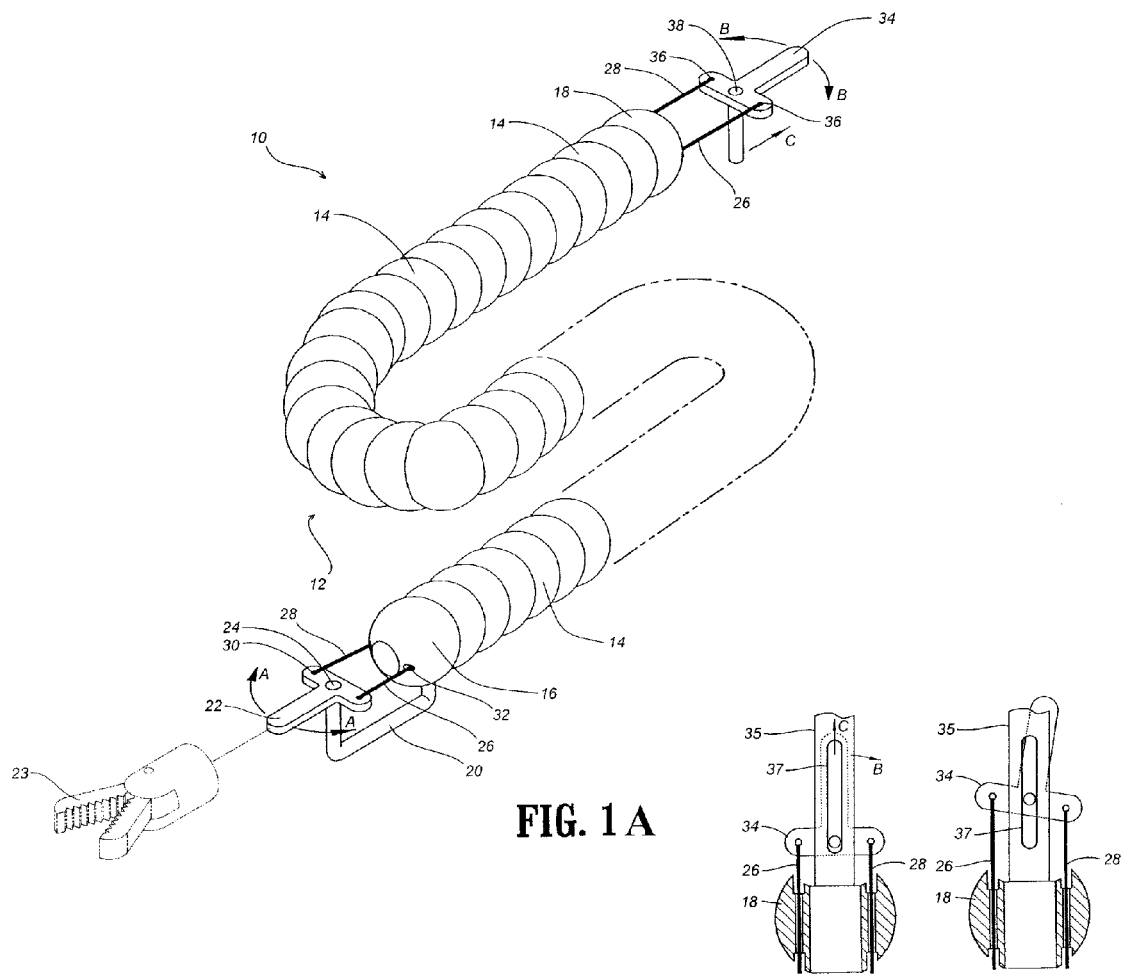
FIG. 1A is a perspective view of a flexible steerable instrument according to one illustrative embodiment of the disclosure.
FIG. 1B is a bottom partial-cross sectional view of a proximal portion of the flexible steerable instrument shown in FIG. 1A further depicting a handle.
FIG. 1C is a view similar to FIG. 1B depicting the proximal bell crank moved to an alternate position with respect to the handle.

Embodiments of the present disclosure will be described herein below with reference to the accompanying drawings. In the following description, well-known functions or constructions are not described in detail to avoid obscuring the present disclosure in unnecessary detail. In the drawings and in the description that follows, the term "proximal," as is traditional, will refer to the direction toward the operator or a relative position on the surgical device or instrument that is closer to the operator, while the term "distal" will refer to the direction away from the operator or relative position of the instrument that is further from the operator.

Referring initially to FIG. 1A, a flexible steerable apparatus 10 includes an elongated flexible carrier body 12 comprising a plurality of interconnected segments 14 including a leading segment 16 and a trailing segment 18. Each segment 14 is configured to pivot relative to neighboring segments 14 allowing the apparatus to assume a linear configuration (FIG. 2), a serpentine path (FIG. 1A) or any configuration therebetween. A support member 20 is fixedly attached between the leading segment 16 and a distal bell crank 22 such that no relative motion between these components is readily achieved. In other embodiments, the support member 20 may be allowed to pivot with respect to the leading segment 16. An end effector 23, which may be supported on or by of formed integrally with distal bell crank 22 is located at a distal end of the apparatus. End effector 23 may include a variety of implements such as grasping jaws, cutting tools, camera, suction attachments etc. Distal bell crank 22 is pivotally attached to support member 20 such that pivotal motion of bell crank 22 about independent pivot 24 may be achieved as indicated by the arrows marked "A." Generally, a bell crank is a mechanism characterized for changing motion about a 90 degree angle. Here, distal bell crank 22 assumes a general T-shape. Alternatively, other configurations are envisioned.

Tensile elements such as tensile members 26, 28 are pivotally attached at one end to distal bell crank 22 at attachment points 30 which are substantially spaced radially outwardly of independent pivot 24. Tensile members 26, 28 are slidably disposed through bores 32 in each of the segments 14. An opposite end of each tensile member 26, 28 is pivotally attached to a control member, which may include a proximal bell crank 34, at attachment points 36. Tensile members 26, 28 may be formed from wires which are substantially inelastic, or alternatively, an elastic material may be used to bias segments 14 into a light contact with one another.

Proximal bell crank 34 is configured to pivot about independent pivot 38 as indicated by arrows marked "B." Proximal bell crank 34 is also configured for longitudinal motion with respect to trailing segment 18 as indicated by arrow "C." Some type of connecting member, may be incorporated to connect the trailing segment 18 to the proximal bell crank 34 that allows the proximal bell crank 34 to slide in the direction of arrow "C" thereby separating the proximal bell crank 34 from the trailing segment 18. The connecting mechanism may include an elongated component which supports the proximal bell crank 34 at a position spaced from the trailing segment 18 and allows the proximal bell crank 34 to pivot and move axially in relation to the elongated component. For example, a suitable connecting member may include a handle 35 having a slot 37 as depicted in FIG. 1B. Handle 35 allows for proximal bell crank to move, for example, in the directions of arrows "B" and "C" to assume to position depicted in FIG. 1C.

Now with reference to FIGS. 2 and 3, steerable instrument 10 is shown in partial cross section to reveal further characteristics. As shown, segments 14 are arranged in a linear fashion such that steerable instrument 10 assumes a straight path. A space 40 between each segment 14 indicates that the tensile members 26, 28 are in limited tension and carrier body 12 is in a flexible state where the segments 14 may pivot relative to one another. Each segment 14 includes a central through bore 42. In combination, the through bores 42 define a central channel 44 through the carrier body 12. Central channel 44 may provide a conduit through which various devices such as, for example camera equipment may be passed.

As best seen in FIG. 4, each segment 14 has a generally spherical shape with a concave surface 46 on its proximal side and a convex surface 48 on its distal side. The segments 14 mechanically interface with one another by mating the concave surface 46 of one segment with the convex surface 48 of the immediately proximal segment 14. This allows the segments 14 to pivot with respect to each other in a ball-joint fashion. In other embodiments, the segments 14 may have, for example, a generally cylindrical shape with the concave and convex surfaces 46, 48 retained on the proximal and distal ends to allow for ball-joint mating. The segments 14 may be formed from medical grade materials such as stainless steel, thermoplastics, titanium or the like.

Now with reference to FIGS. 5 through 8 the operation of steerable apparatus 10 will be described. The apparatus may be advanced into a body cavity such as the bowel of a patient in a distal direction such that the distal bell crank 22 with a tool supported on or formed integrally therewith is disposed within the body cavity. The proximal bell crank 34 remains outside the patient where it may be handled by an operator such as a clinician. The clinician may impart a force on proximal bell crank 34 as indicated by arrow "D" in FIG. 5. This causes the proximal bell crank 34 to pivot about independent pivot 38 drawing tensile member 26 in a proximal direction thus increasing the tension in tensile member 26 while relaxing the tension in tensile member 28. The resulting differential tension in tensile members 26, 28 causes the flexible carrier body 12 to curve in the direction of the greater tension as the segments 14 pivot relative to one another. Also, this differential tension causes distal bell crank 22 to pivot about independent pivot 24 as represented by arrow "E." Likewise, the clinician may impart a force on proximal bell crank 34 in the direction of arrow "F" (FIG. 6) to cause the flexible carrier body 12 to curve in the opposite direction and the distal bell crank 22 to pivot in the direction of arrow "G" (FIG. 6). In this way, the clinician may steer the apparatus 10 as it is advanced through the body cavity to a satisfactory position.

Once the apparatus 10 has achieved a satisfactory position, the clinician may rigidize the carrier body 12, i.e. increase the friction between segments 14 to maintain the position and configuration of the carrier body 12, by imparting a force on the proximal bell crank 34 in the direction of arrow "H" depicted in FIG. 7. This causes the proximal bell crank 34 to move in a proximal direction with respect to trailing segment 18. This motion is first carried through tensile members 26, 28, establishing a general tension therein, to distal bell crank 22, and then on to support member 20, on to leading segment 16 and finally on to each successive segment 14 until trailing segment 18 which remains in place. Again, trailing segment 18 is held in place due to a connection mechanism (not shown). This relative motion causes the segments 14 to converge in the direction indicated by arrows "J" as each is drawn toward trailing segment 18. This convergence creates high frictional forces between the interfacing concave 46 and convex 48 surfaces of segments 14 that rigidize the carrier body 12. In this rigidized condition, the carrier body 12 will maintain its position and configuration providing a relatively stable platform for the manipulation of tissue. The stabilization allows for greater forces to be developed for pushing, pulling, twisting or general manipulation of targeted tissue.

Once the apparatus 10 has achieved a rigidized condition, the proximal bell crank 34 may be further pivoted in either direction to cause a corresponding pivot in the distal bell crank 22. Because the distal bell crank 22 is not subject to the high frictional forces associated with the segments 14, it will be free to pivot upon an application of a differential tension in tensile members 26, 28. The general tension in tensile members 26, 28 that causes the carrier body 12 to assume a rigid condition is defined by the position of proximal bell crank 34 in the direction of arrow "C" (FIG. 1A) or "H" (FIG. 7). This general tension is not substantially diminished when, for example, a differential tension is applied by pivoting the proximal bell crank 34. In this way, an operator may manipulate an end effector of an instrument in a rigid condition using the same control member in the same manner as in steering the instrument into position when in a flexible condition.

Other embodiments are envisioned in which multiple pairs of tensile elements similar to tensile members 26, 28 may be used to both rigidize the carrier body 12 and manipulate an end effector or distal tool. For example, a second pair of tensile elements (not shown) may be placed at a 90 degree angle from tensile members 26, 28 to establish an X-Y or multiple-degree-of-freedom steering system when attached to the end effector. A second pivot may be substantially orthogonal to pivot 24 to accommodate such a steering system. Yet another pair of tensile elements could cause a rotation at the distal end. Also, additional tensile members (not shown) may be incorporated to operate end effectors such as graspers, scissors, biopsy pincers and the like. Furthermore, these conventional types of end effectors may be coupled to an end effector such as distal bell crank 22 to allow some degree of motion once the apparatus has achieved a rigid condition.

Although the foregoing disclosure has been described in some detail by way of illustration and example, for purposes of clarity or understanding, certain changes and modifications may be practiced within the scope of the appended claims.

What is claimed is:

1. An apparatus for insertion into a body cavity comprising:
    an elongated body including a distal end, a proximal end and a length therebetween defining an axis, at least a portion of the distal end of the elongated body being flexible;
    an end effector disposed at the distal end of the elongated body;
    a support member interconnecting the end effector to the distal end of the elongated body;
    a pair of tensile elements extending from the proximal end of the elongated body to the distal end of the elongated body and coupled to the end effector; and
    a control member coupled to a proximal end of the tensile elements, the control member being operable to impart tension in each of the tensile elements to change the flexible portion of the elongated body to a substantially rigid condition, and wherein the control member is operable to move the end effector independently of the flexible portion of the elongated body when the flexible portion of the elongated body is in the rigid condition by varying the tension in one of the tensile elements in relation to tension in the other of the tensile elements.

2. The apparatus according to claim 1, wherein the control member is operable to move the end effector pivotally about a first pivot.

3. The apparatus according to claim 1, wherein the control member comprises a bell crank coupled to the pair of tensile elements such that pivotal motion in the control member varies the tension in one of the tensile elements in relation to tension in the other of the tensile elements.

4. The apparatus according to claim 1, wherein the flexible portion of the elongated body comprises a plurality of interconnected segments configured to pivot relative to one another, the plurality of interconnected segments including a leading segment adjacent the distal end of the elongated body, and a trailing segment proximal of the leading segment.

5. The apparatus according to claim 4, wherein the support member is fixedly coupled to the leading segment and pivotally coupled to the end effector.

6. The apparatus according to claim 4, wherein at least one of the plurality of interconnected segments has a substantially spherical shape and includes a concave surface adapted to accommodate a convex surface of a neighboring segment.

7. The apparatus according to claim 4, wherein each of the plurality of interconnected segments includes a cavity therein such that a common channel is defined through the flexible portion of the elongated body.

8. The apparatus according to claim 2, further comprising a second pair of tensile elements coupled to the end effector and the control member, the control member operable to move the end effector pivotally about a second pivot, the second pivot being substantially orthogonal to the first pivot.

9. A flexible steerable apparatus comprising:
    an elongated body defining one or more longitudinally extending cavities therein, at least a portion of a distal end of the elongated body being flexible;
    an end effector disposed at the distal end of the elongated body;
    a pair of tensile elements extending from a proximal end of the elongated body to the distal end of the body and coupled to the end effector; and
    a control member coupled to a proximal end of the tensile elements, the control member being operable to impart tension in each of the tensile elements to change the flexible portion of the elongated body to a substantially rigid condition, and wherein the control member is operable to move the end effector independently of the flexible portion of the elongated body when the flexible portion of the elongated body is in the rigid condition by varying the tension in one of the tensile elements in relation to tension in the other of the tensile elements.

10. A method for manipulating internal tissue of a patient, the method comprising the steps of:
    inserting an end effector disposed at a distal end of an at least partially flexible instrument into a body cavity of the patient;
    modifying the orientation of the distal end of the instrument by using a control member disposed on a proximal end of the instrument to impart a differential tension to a pair of tensile elements coupled to the end effector to steer the end effector into proximity with targeted tissue; and shifting the instrument from a flexible condition to a substantially rigid condition with the end effector in proximity to targeted tissue by using the control member to impart a general tension to the pair of tensile elements; and manipulating the control member to alter the orientation of the end effector when the instrument is in the substantially rigid condition to impart a differential tension to the pair of tensile elements to move the end effector to contact the targeted tissue.

11. The apparatus according to claim 1, wherein a space is defined between the end effector and the distal end of the elongated body.

12. The apparatus according to claim 1, wherein the control member is configured for translation relative to the elongated body.

13. The apparatus according to claim 1, wherein the support member is pivotable relative to the elongated body.

* * * * *